(12) United States Patent
Xu (10) Patent No.: US 6,873,725 B2
(45) Date of Patent: Mar. 29, 2005

(54) SIMULTANEOUS MEASUREMENT AND DISPLAY OF 3-D SIZE DISTRIBUTIONS OF PARTICULATE MATERIALS IN SUSPENSIONS

(75) Inventor: Renliang Xu, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 30 days.

(21) Appl. No.: 10/237,369

(22) Filed: Sep. 9, 2002

(65) Prior Publication Data

US 2004/0047502 A1 Mar. 11, 2004

(51) Int. Cl.[7] .................................................. G06K 9/00
(52) U.S. Cl. ........................ 382/154; 382/214; 382/286; 356/335; 702/21; 702/128; 73/865.5
(58) Field of Search ........................... 382/154; 345/419, 345/420, 421, 422, 581; 356/12

(56) References Cited

U.S. PATENT DOCUMENTS

| | | | |
|---|---|---|---|
| 4,097,845 A | 6/1978 | Bacus | |
| 4,175,860 A | 11/1979 | Bacus | |
| 4,338,024 A | 7/1982 | Bolz et al. | |
| 4,538,299 A | 8/1985 | DeForest | |
| 4,817,446 A | 4/1989 | Kanamori | |
| 5,268,966 A | 12/1993 | Kasdan | |
| 5,497,232 A | * 3/1996 | Watano et al. | ............... 356/335 |
| 5,655,028 A | * 8/1997 | Soll et al. | ................... 382/133 |
| 6,266,137 B1 | * 7/2001 | Morinaga | ................ 356/237.1 |
| 6,317,511 B1 | * 11/2001 | Horiuchi | ..................... 382/133 |
| 6,583,865 B2 | * 6/2003 | Basiji et al. | .................. 356/73 |
| 6,590,646 B2 | * 7/2003 | Kasdan et al. | .............. 356/246 |
| 6,633,368 B2 | * 10/2003 | Berndt | ........................ 356/39 |

OTHER PUBLICATIONS

RapidVUE™ Particle Shape and Size Analyzer Product Overview and Specifications from http://www.beckman-coulter.com, ©1998–2002 Beckman Coulter, Inc.

* cited by examiner

Primary Examiner—Samir Ahmed
Assistant Examiner—Anand Bhatnagar
(74) Attorney, Agent, or Firm—Howson and Howson; Mitchell E. Alter (57) ABSTRACT

An apparatus and method in which a still image, or still images, are obtained of a plurality of particles suspended in a fluid medium. Each still image is transferred to an image analyzing unit that measures a set of dimensional characteristics per particle for particles appearing in the image and determine an occurrence characteristic for particles having a matching set of dimensional characteristics. Preferably, a three dimensional representation of the characteristics is displayed in real time. More preferably, the displayed three-dimensional representation is continuously updated and further entries are accumulated on the display as image analysis is performed. The display provides information to a viewer enabling the viewer to determine a shape distribution of the particles within the suspension even when multiple particle shapes are present.

22 Claims, 6 Drawing Sheets

SIMULTANEOUS MEASUREMENT AND DISPLAY OF 3-D SIZE DISTRIBUTIONS OF PARTICULATE MATERIALS IN SUSPENSIONS

FIELD OF THE INVENTION

The present invention relates to an apparatus and method for measuring and displaying a three dimensional size distribution of particles contained in a suspension, and more particularly, the present invention relates to an apparatus and method for presenting to a viewer a display which enables the viewer to quickly determine a size distribution of the particles within the suspension.

BACKGROUND OF THE INVENTION

Research and development of new products and techniques and quality control of existing products and techniques in many industries require the task of determining various characteristics, including for example dimensional characteristics, of particles a few millimeters or less in size. Typically, the particles are suspended in air or a liquid medium, and the size and shape of the particles vary greatly within a given sample of the suspension. For example, the various shapes may include substantially spherical, rod-shaped and plate-shaped particles to name a few. Thus, due to the disparity of particle sizes and shapes within a sample of the suspension, the size and shape characteristics of many, if not all, particles must be accessed to obtain a meaningful statistical representation of the actual size distribution of the particles in the suspension.

Conventional technologies for measuring the size of particles in a suspension include ensemble and non-ensemble technologies. In the so-called ensemble technology, signals from multiple particles are simultaneously detected and recorded as a single variable. Thereafter, an appropriate theoretical model is utilized to provide estimated size information inferred from the variable as recorded in various different experimental configurations. In such a technology, the determination of more than one parameter is difficult and generally cannot be accomplished, and size is typically represented as a single parameter, such as, a mean value or a distribution.

In a so-called non-ensemble technology, particles within a sample of the suspension are analyzed one at a time and a signal is detected from each individual particle. For instance, individual particles can be analyzed electronically based on the Coulter Principle in which size is determined by the change of electrical impedance measured while a particle passes between a pair of electrodes. Other examples of methods for analyzing the size of individual particles include optical methods using a single optical particle counter, aerodynamic methods in which time-of-flight is measured, and microscopic image analysis methods utilizing electronically or optically obtained images. Except for the image analysis method, the conventional non-ensemble technologies can be used only to provide a single size parameter, typically in the form of equivalent sphere diameter. In addition, many of the above referenced technologies produce a size parameter based strictly on the assumption that the shape of each particle within the suspension is a perfect sphere. Thus, any deviation of particle shape from that of a sphere produces errors or bias in the results of the particle size determination.

Most conventional techniques produce unsatisfactory results when analyzing the size distribution of particles that are non-spherical, particularly when at least some of the particles have extreme shapes such as rod-like or plate-like shapes. Thus, the determined size distribution often does not accurately reflect the actual size distribution of particles within a given sample of a suspension, and with respect to quality control issues, such techniques are not sufficiently sensitive to detect changes in the sizes and shapes of particles that may exist from one sample to the next. Further, a single size parameter utilized to represent sizes of particles in a sample clearly no longer meets the needs of current particle research, development, production and quality control. The conventional technology often uses a selected pre-defined size distribution or some other statistically calculated size distribution that does not reflect the actual size distribution of the particles.

Determining a true size distribution has become particularly critical in some industries, such as the pharmaceutical industry where the determination of size distribution utilizing dual parameters instead of a single parameter is preferred and desired. Traditional image analysis, referenced above, provides a two-dimensional analysis for each particle imaged in a fixed projection. However, the required particle orientation, sample preparation, time consumption, and expense of conventional microscopic technologies limit their application in daily research and development and quality control operations.

Examples of some known image analysis systems and systems for determining particle size distributions are disclosed in U.S. Pat. Nos.: 4,097,845 and 4,175,860 issued to Bacus; U.S. Pat. No. 4,338,024 issued to Bolz et al.; U.S. Pat. No. 4,538,299 issued to DeForest; U.S. Pat. No. 4,817,446 issued to Kanamori; U.S. Pat. No. 5,268,966 issued to Kasdan; U.S. Pat. No. 5,655,028 issued to Soll et al.; and U.S. Pat. No. 6,317,511 issued to Horiuchi. In addition, see U.S. patent application Ser. No. 09/677,076 which was filed on Sep. 29, 2000 and which is assigned to the assignee of the present application, and see the commercially available RapidVUE™ particle shape and size analyzer marketed by Beckman Coulter, Inc., Miami, Fla.

Although the aforementioned apparatus, methods, systems and techniques can function satisfactorily for their intended purposes, there exists a need for an apparatus and method which can accurately determine size distribution of particles within a sample of a suspension and which are capable of expressing the size distribution in a manner that readily conveys the information to an intended person. Preferably, the apparatus and method should rapidly measure and determine the shape and size of each individual particle within an image and should simultaneously display the information in real time. In addition, preferably the expression of the results should be presented to a viewer in a display enabling the viewer to quickly, if not substantially instantaneously, determine the actual distribution of particle shapes and sizes within the sample. The display unit can be a printer which prints the dimensional representation or a display screen. Further, preferably the apparatus and method should be capable of use in daily operations, should be cost effective, and should require only a minimum of skill to operate, utilize and maintain.

With the foregoing in mind, a primary object of the present invention is to provide an apparatus and method that accurately determine the actual shape and size of particles within a sample of a suspension.

Another object of the present invention is to provide an apparatus and method that are capable of expressing the actual shape and size distribution of the particles in a manner that readily conveys such information to an intended entity.

A further object of the present invention is to provide an apparatus and method that rapidly measure and determine the shape and size of each individual particle within an image and that simultaneously display the information in real time.

A still further object of the present invention is to provide an apparatus and method that provide a visual display to an intended viewer enabling the viewer to quickly, if not substantially instantaneously, determine the actual distribution of particle shapes and sizes within an analyzed sample.

Yet another object of the present invention is to provide an apparatus that is capable of use in daily operations in a cost efficient manner requiring only a minimum of skill to operate, utilize and maintain.

SUMMARY OF THE INVENTION

According to one aspect of the present invention, an apparatus for analyzing particles suspended in a fluid medium is provided. The apparatus includes an image detector for obtaining at least one still image of a plurality of particles suspended in the fluid medium and an image analyzing unit for measuring a set of at least two dimensional characteristics per particle for particles appearing in the still image and for comparing the measured sets of dimensional characteristics to determine an occurrence characteristic of particles having a matching set of dimensional characteristics. In addition, the apparatus includes a display unit that presents a representation of the above referenced characteristics in a manner enabling an intended entity to determine the shape distribution of particles appearing in the still image, or images. Preferably, the representation is a three dimensional (3-D) representation providing information about the particles in a manner which permits a viewer to readily determine a shape and size distribution of the particles.

Preferably, the display unit has a screen on which a three dimensional graphical representation is provided as an x-y-z coordinate plot, wherein a pair of the coordinates correspond to the particle dimensional characteristics and a third coordinate corresponds to the occurrence characteristic. The dimensional characteristics preferably include at least one of particle length, width, depth, diameter, sphericity, and aspect ratio. The occurrence characteristic are values representing an occurrence of particles having a given set of dimensional characteristics measured in terms of particle number, area, volume, length, width, depth, diameter, sphericity or aspect ratio. In addition, preferably the plot is continually updated in real-time and continues to accumulate and display further particle information as the still image, or still images, are processed by the image analyzing unit. Further, preferably the image analyzing unit forms and stores a matrix table of data including the dimensional characteristics and the occurrence characteristic so that individual characteristics of each particle are saved and capable of subsequent representation.

According to one embodiment of the apparatus of the present invention, the image analyzing unit is a computer having at least one image analysis computer software program that analyzes the still image, measures the dimensions of the particles, determines the occurrence of particles having a given set of dimensions, forms the matrix table, and causes the three dimensional representation to be displayed on the display unit. In addition, the apparatus of the preferred embodiment includes a flow cell which provides a path of flow for particles suspended in a fluid and which defines a chamber in which the still image is obtained by the image detector. Still further, the image detector of the preferred embodiment is a camera for obtaining optical images of the particles suspended in the fluid.

According to another aspect of the present invention, a method of analyzing particles suspended in a fluid medium is provided. The method includes the steps of obtaining a still image of a plurality of particles suspended in a fluid medium, measuring at least two dimensional characteristics per particle for particles appearing in the image, and comparing the measured dimensional characteristics to determine an occurrence characteristic of particles having given dimensional characteristics. In addition, the method includes the step of displaying a three dimensional representation of the characteristics. The three dimensional representation has three coordinates with a pair of the coordinates corresponding to the particle dimensional characteristics and a third coordinate corresponding to the occurrence characteristic. The three dimensional representation provides information on the particles in a manner which permits a viewer of the display to determine a shape distribution of the particles appearing in the image.

Preferably, the measuring step is performed by at least one image analysis computer program immediately after the still image is obtained, and the comparing and displaying steps occur simultaneously with the measuring step such that the three dimensional representation is updated in real time as the image analysis computer program determines the particle characteristics. In addition, preferably the computer program creates and stores a matrix table providing retrievable dimension information for each particle appearing in the still image so that the three dimensional representation represents actual measured size and shape information of the particles.

BRIEF DESCRIPTION OF THE DRAWINGS

The foregoing and other objects, features and advantages of the present invention should become apparent from the following description when taken in conjunction with the accompanying drawing, in which.

DETAILED DESCRIPTION OF THE PREFERRED EMBODIMENT

Figure 1:
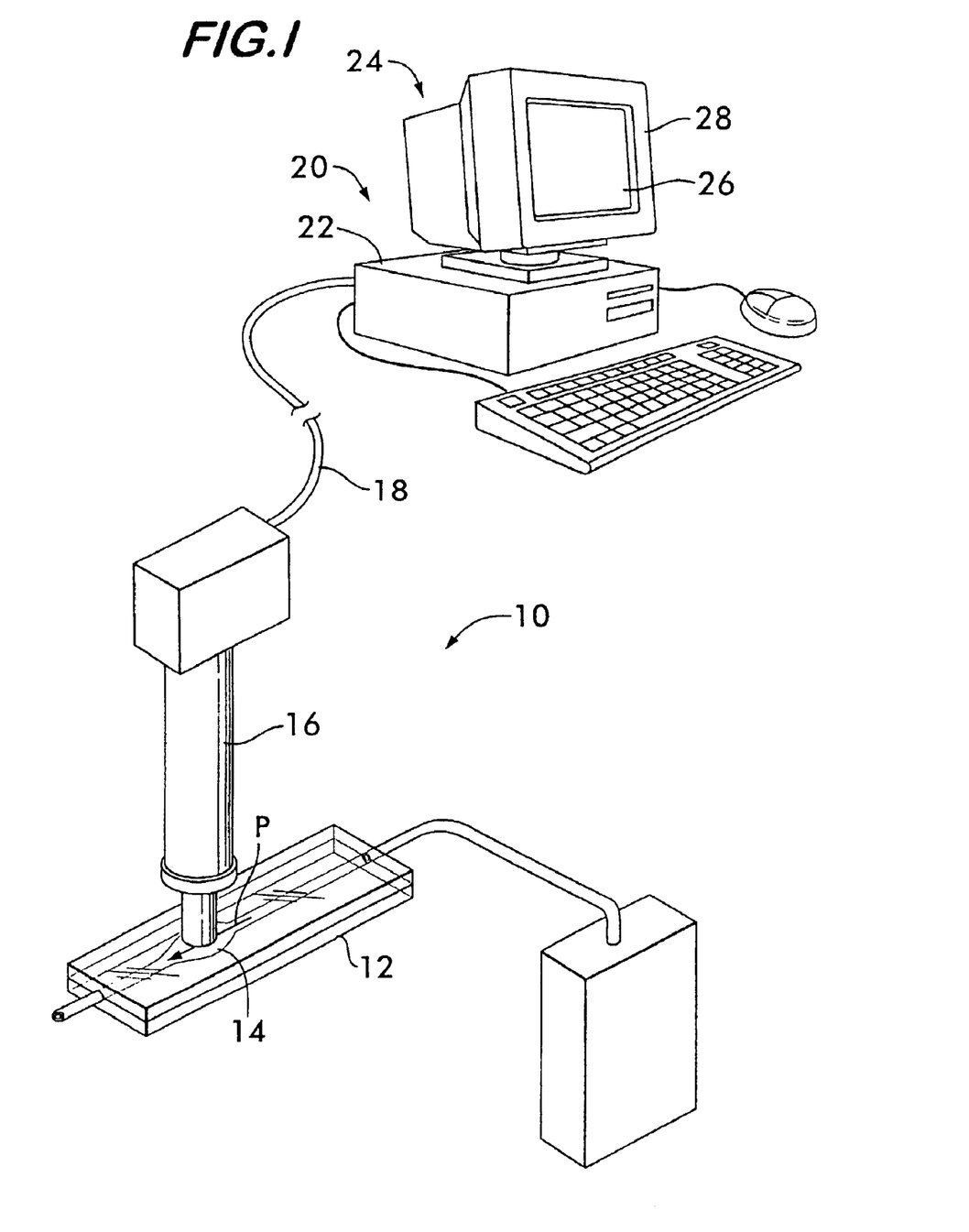
FIG. 1 is a perspective view of an example of a dynamic image analyzing system according to the present invention.

FIG. 1 illustrates an example of a set up of a particle analysis apparatus 10 according to the present invention. The apparatus 10 captures images of particles suspended in a fluid medium, analyzes the images, and then presents a representation of the size and shape of the particles appearing in the image. As will be described in greater detail, the apparatus 10 processes the particle size and shape information such that the apparatus 10 can readily convey particle shape and size information to an intended entity, person or audience in a manner which permits the entity, person, or audience to quickly comprehend the actual measured size and shape distribution of particles within the analyzed sample. The apparatus and method can provide both shape distribution and size distribution of the particles suspended in a media.

As illustrated in FIG. 1, for example, a flow cell 12 or like device is utilized to define a chamber 14 and a path of flow "P" of a plurality of particles suspended in a fluid medium, such as, a gas, air, a liquid or the like. A strobe light (not shown), or other light source, is utilized to produce a beam of light that is preferably expanded to a thick homogenous beam before it impinges on the chamber 14. An image detector, camera or the like, 16 is synchronized with the light source to capture an image of the particles within the chamber 14. The image detector 16 can be a CCD camera or any other device for optically or electronically capturing an image.

The image itself can be of various formats, as desired. For instance, the particles appearing in the image can be taken from: (i) non-focused in a still fluid (for example, free falling); (ii) focused in a still fluid (for example, injection); (iii) non-focused in a moving fluid (for example, circulation or tube flow); (iv) focused in a moving fluid (for example, sheath flow in a liquid); and (v) a stopped flow image. In any of these formats, images are taken as two-dimensional projections of particles and are preferably taken perpendicularly of the direction of the beam of light.

After the image is taken by the image detector 16, it is transferred via a communication link 18 to an image analyzing unit 20. In FIG. 1, the image analyzing unit 20 is illustrated as a computer 22 that has at least one program including an image analysis software program. The information obtained by the image analyzing unit 20 is displayed on a display unit 24. In the illustrated embodiment, the display unit 24 is a screen 26 of a monitor 28 forming part of the computer 22. Of course, the display unit 24 can be any other device for displaying information and is not required to form a part of the image analysis unit 20. For example, the display unit can be a printer for printing the information.

In the prior art as previously discussed, the results of the analyzed image are presented either using a single dimensional parameter such as an equivalent circular diameter or two parameters such as a long dimension (for example, length) and a short dimension (for example, width). In the former case, a distribution of particle diameter is obtained. In the latter case, two distributions are obtained which are a length distribution and a width distribution. However, in the latter case, any correlation between the length and width measurements of a particle is not preserved, saved or represented. Thus, the distribution of particle shape cannot be determined or accessed.

In contrast, the image analyzing unit 20 according to the present invention forms a matrix table or like data storage format that includes and correlates at least two corresponding dimensional characteristics for each entry such that, for instance, a correlation between the actual measured length and width of each particle is saved and retrievable. The dimensional characteristics, or parameters, can include, for example, particle length, width, depth, equivalent diameter, sphericity, and aspect ratio and can be represented using various conventions such as Feret length, Krommbien length, and other conventions known to those skilled in the art. Thus, a set of dimensional characteristics, including at least two dimensions of a particle, is measured and preserved by the image analyzing unit 20. This stored information can be utilized to determine whether or not individual or subsets of particles within a sample are spherical, non-spherical, rod-shaped, plate-shaped, or some other definable shape.

The image analyzing unit 20 also compares the measured sets of dimensional characteristics to determine at least one additional characteristic, or parameter, for each given set of dimensional characteristics. The additional characteristic can be a dimensional or an occurrence characteristic. Thus, for each entry in the matrix table, there are at least two dimensional characteristics and at least one additional characteristic for a total of a minimum of three characteristics.

The additional characteristic is preferably an occurrence characteristic. For example, the occurrence characteristic can be the total number of particles that appear in the still images and that are of a given size and shape. Alternatively, the occurrence characteristic can be represented as a value relating to the occurrence of volume or area of particles having a given set of dimensional characteristics. Further, the occurrence characteristic can be represented as a value relating to the occurrence of total particle length, width, depth, equivalent diameter, sphericity, or aspect ratio of particles of a given size and shape. Still further, other occurrence characteristics can be determined for each set of dimensional characteristics.

The characteristics stored in the matrix table are utilized to create a three dimensional representation on the display unit 24. See, for instance, FIGS. 4 and 6 which are three-dimensional graphical representations according to the present invention. Alternatively, the results can be represented in tabular form including at least three columns. Preferably, the representation is on x, y and z coordinates with a pair of coordinates corresponding to a pair of dimensional characteristics stored in the matrix table and with one of the coordinates corresponding to the additional characteristic. Thus, as demonstrated in the Examples discussed below, particle shape and size information is preserved and presented to a viewer with extreme clarity and resolution enabling the viewer to quickly, if not substantially instantaneously, comprehend and determine the shape and size distribution of particles within the analyzed sample.

EXAMPLE NO. 1

A dynamic image analysis measurement was performed on a sample having a plurality of fibrous particles suspended in a fluid medium. Presentations were prepared according to prior art techniques (FIGS. 2 and 3) and according to the present invention (FIG. 4).

Figure 2:
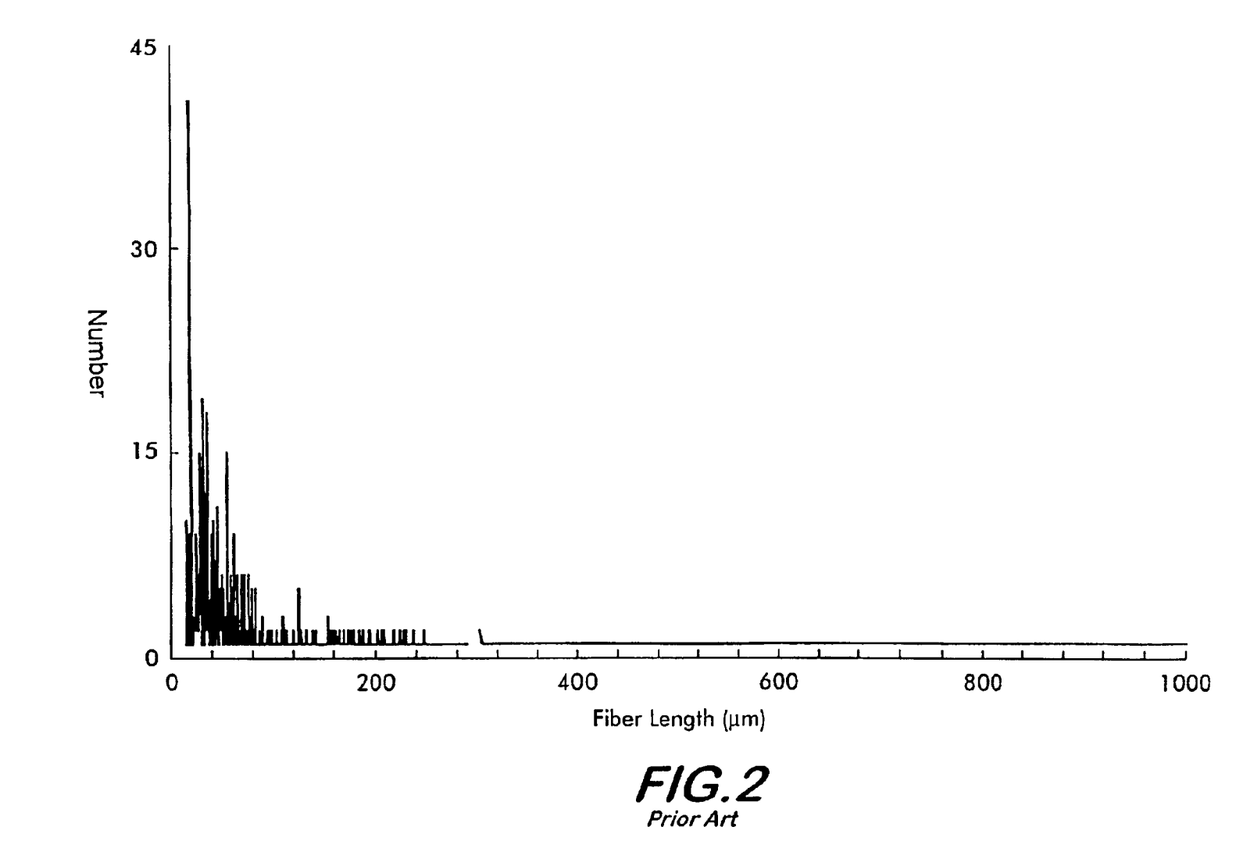
FIG. 2 is a two-dimensional display of a particle analysis of the length of fibrous particles obtained and displayed according to prior art techniques.
Figure 3:
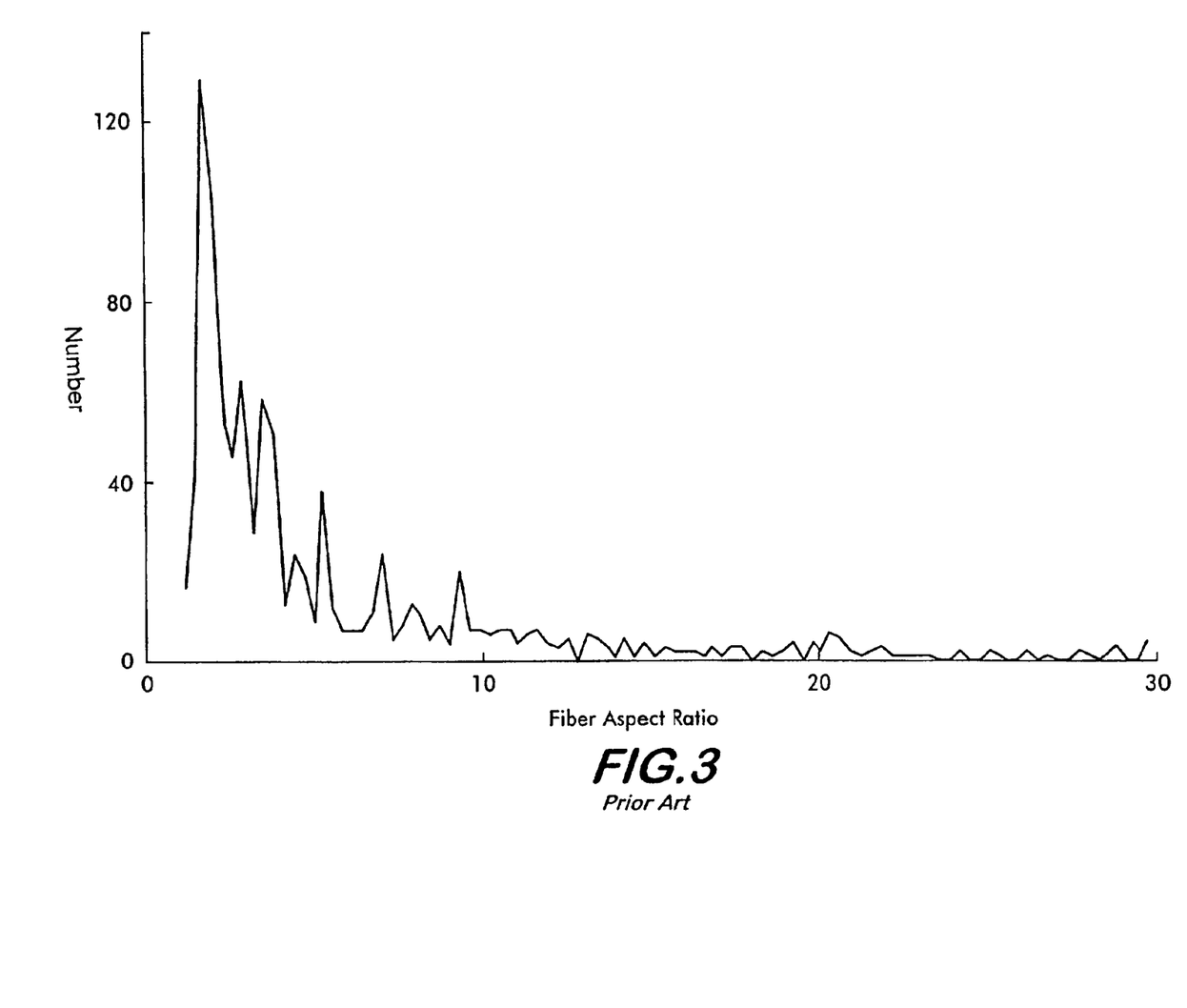
FIG. 3 is a two-dimensional display of a particle analysis of the aspect ratio of fibrous particles obtained and displayed according to prior art techniques.

FIG. 2 is a two dimensional graph with the x-axis corresponding to fiber length and the y-axis corresponding to the number of occurrences of each particular fiber length. It discloses that the fibers in the sample are of a length ranging between about 0 to 300 $\mu$m and that the majority are less than about 80 $\mu$m. FIG. 3 is a two dimensional graph with the x-axis corresponding to fiber aspect ratio and the y-axis corresponding to the number of occurrences of each particular fiber aspect ratio. It discloses that the aspect ratio of the fibers range between about 0 to 30 and that the majority is within a range of about 1 to about 4. However, no further information can be readily determined from the graphs illustrated in FIGS. 2 and 3, and certainly, the graphs do not disclose whether or not the fibers are of similar or different shapes.

According to the present invention, at least two dimensional characteristics are measured per particle for particles appearing in captured images, and an additional occurrence characteristic is determined from the measured dimensional characteristics. More specifically, the first two dimensional characteristics are independent variables and the third characteristic is a dependent variable of at least one of the independent variables. These characteristics are preserved in a matrix table data storage format or the like. Thus, the presentation according to the present invention is in the form of a three dimensional (3-D) representation that readily reveals the shape information of the particles in the sample.

Figure 4:
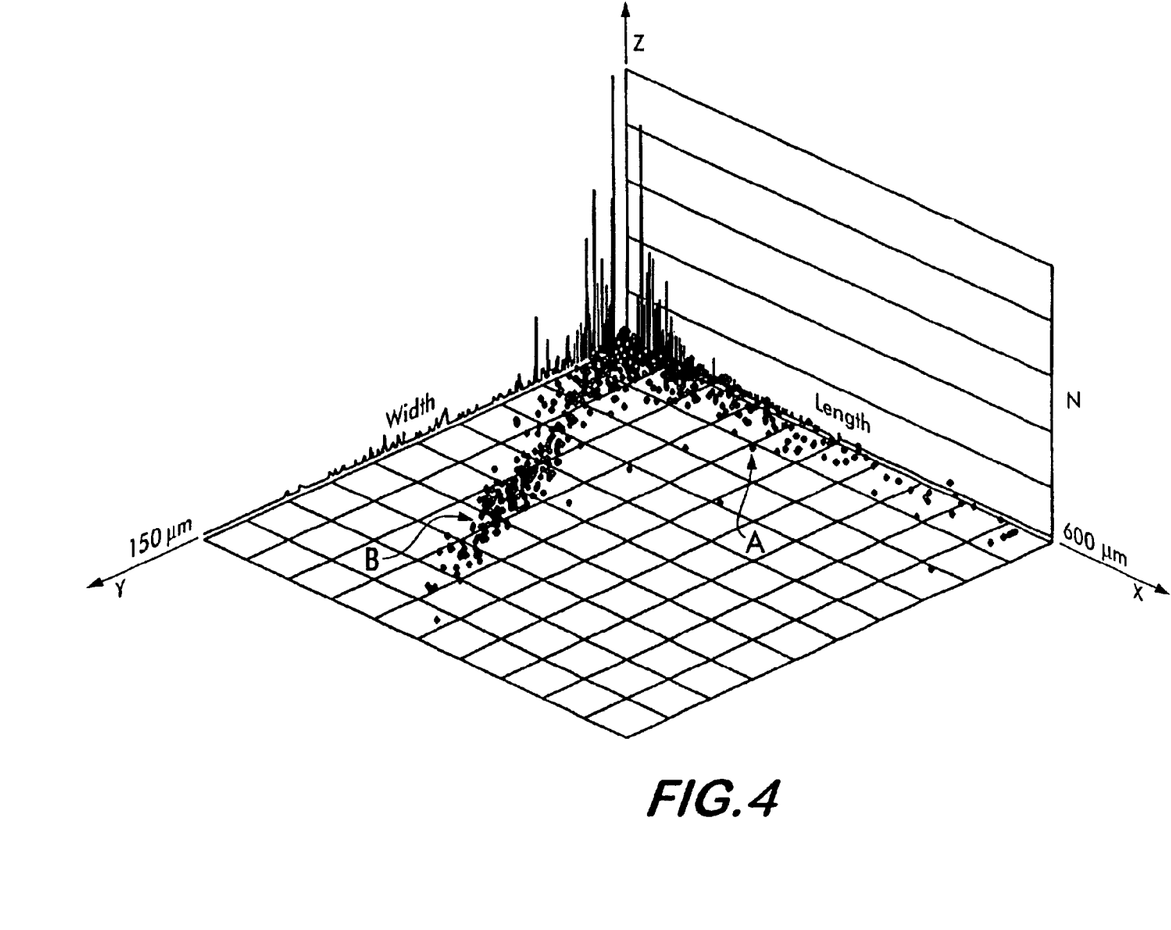
FIG. 4 is a three-dimensional display which is of a particle analysis of a fibrous particle sample corresponding to that of FIGS. 2 and 3 and which readily conveys particle shape information by number of particles according to the present invention.

FIG. 4 provides an example of the representation according to the present invention and is a three dimensional (3-D) plot with one axis, x, corresponding to fiber length; another axis, y, corresponding to fiber width; and a third axis, z, corresponding to a number of occurrences of a particular fiber length and width combination. Thus, this plot provides a particle shape and size distribution by particle number. Entries on the plot correspond to the information stored in the matrix table such that the shape of the particle including its width and length can be illustrated on the graph by a single entry. The distributions on the xy plane and on the yz plane are the width and length distributions that are obtained utilizing conventional image analysis, for instance, as illustrated in FIG. 2. These width and length distributions are the cumulative projections from the three dimensional (3-D) distribution on the respective axial planes. The occurrence value can alternatively relate to a total particle volume of particles having each particular width and length combination, or to some other occurrence value.

A viewer of the plot on FIG. 4 can readily and quickly determine and comprehend that there are two types of fibers within the analyzed sample. One type of fiber identified as subset "A" has similar fiber widths ranging between about 5 to 15 $\mu$m but varying lengths. A second type of fiber identified as subset "B" has a length varying from about 5 to 250 $\mu$m and an aspect ratio of about 2. This information is not provided by the prior art 2-D graphs and cannot be obtained without preserving and correlating multiple measured dimensional characteristics for each particle. In addition, the format of the presentation according to the present invention permits a viewer to quickly realize the existence of the two types of fibers contained within the sample. Obviously, this is important information both for research and development purposes as well as for quality control purposes.

EXAMPLE NO. 2

A dynamic image analysis measurement was performed on a sample having a mixture of glass bead particles suspended in a fluid medium. Presentations were prepared according to prior art techniques (FIG. 5) and according to the present invention (FIG. 6).

Figure 5:
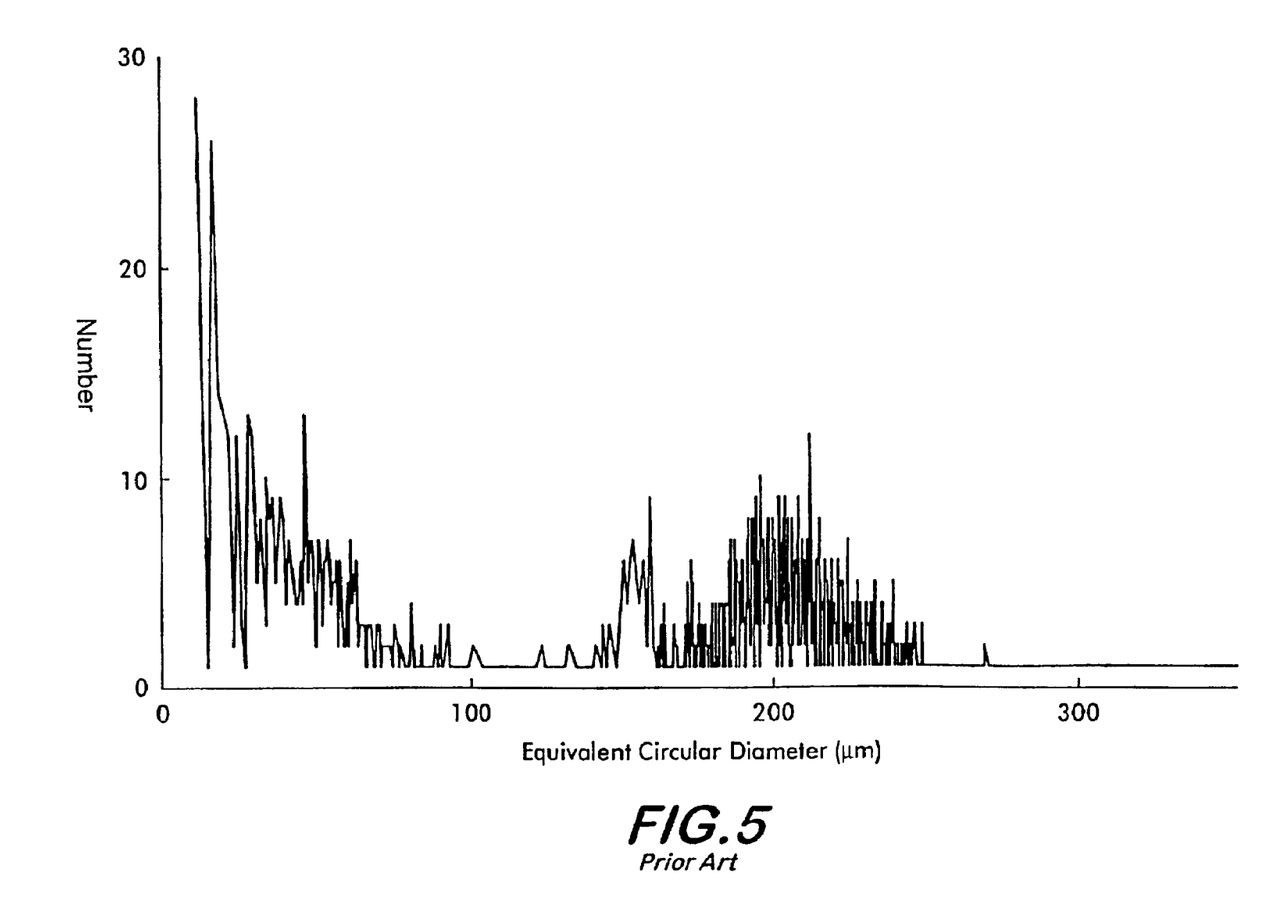
FIG. 5 is a two-dimensional display of a particle analysis of an equivalent circular diameter distribution of a mixture of glass beads according to prior art techniques.

FIG. 5 is a two dimensional graph with the x-axis corresponding to particle equivalent circular diameter and the y-axis corresponding to the number of occurrences of each particular equivalent circular diameter. It discloses the existence of two groups of particles in which one has equivalent circular diameters below about 100 $\mu$m and the other is between about 150 to 250 $\mu$m. However, no further information can readily be determined from the graph.

Figure 6:
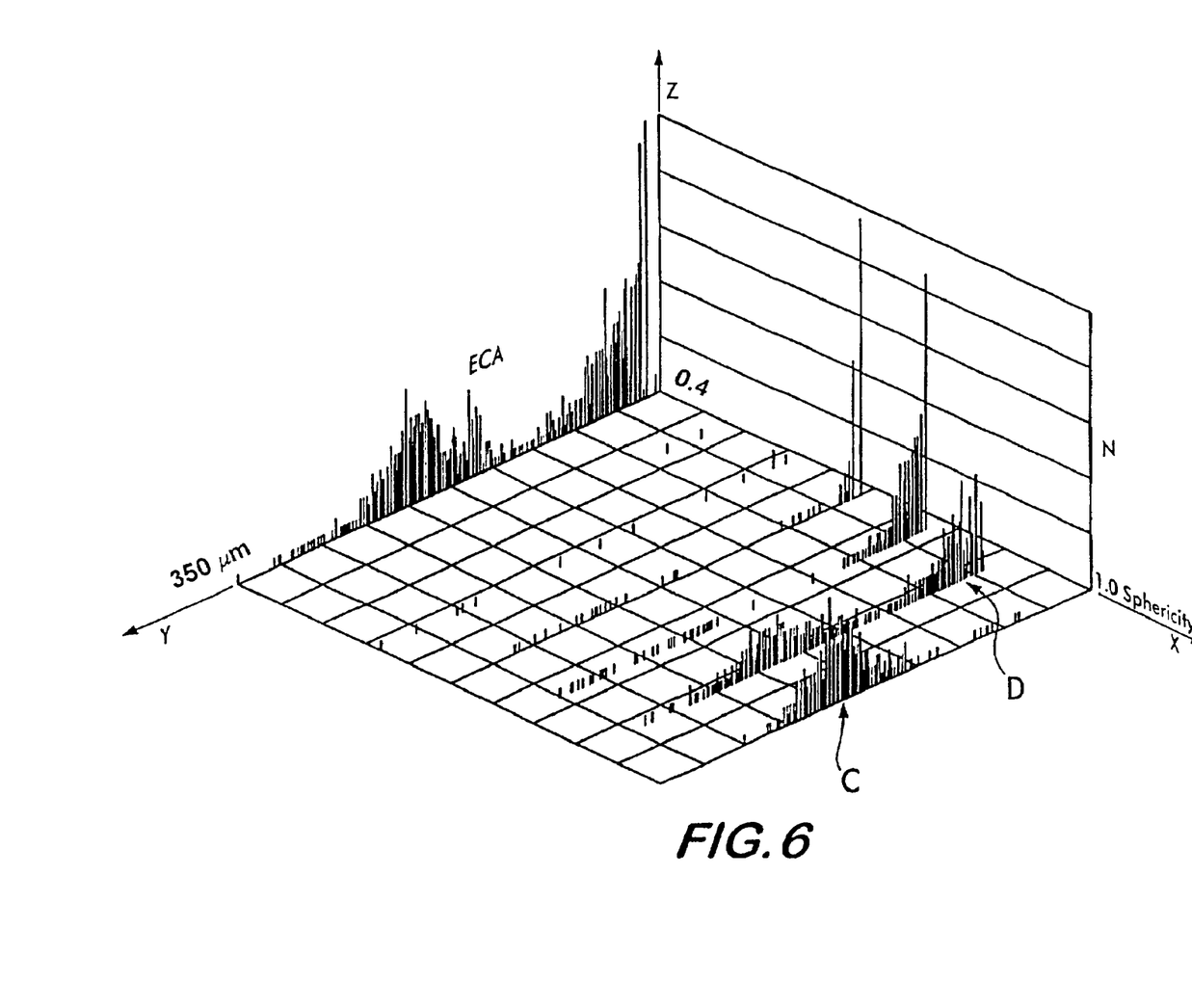
FIG. 6 is a three-dimensional display of a particle analysis of a mixture of glass beads that readily conveys particle shape and size information by sphericity according to the present invention.

FIG. 6 is a 3-D plot according to the present invention with one axis corresponding to an equivalent circular diameter, another axis corresponding to particle sphericity, and a third axis corresponding to the number of occurrences of a particular equivalent circular diameter and sphericity combination. A viewer of the 3-D plot of FIG. 6 can readily and quickly determine that the two groups of particles include larger particles that are close to perfect spheres and smaller particles that have a less perfect spherical shape. For example, the larger particles identified as subset "C" have sphericity values that are greater than about 0.9, and the smaller particles identified as subset "D" have sphericity values of 0.9 and below. This information is not provided by prior art 2-D graphs and cannot be obtained without preserving and correlating multiple measured dimensional characteristics for each particle.

The present invention also provides a method of analyzing particles suspended in a fluid medium. The preferred method requires at least one still image to be obtained of a plurality of particles suspended in a fluid medium. Thereafter, each still image is transferred to an image analyzing unit which measures a set of at least two dimensional characteristics per particle for particles appearing in the image. Preferably, while the dimensional characteristics are measured and stored, the image analyzing unit determines an occurrence characteristic related to the particles having a matching set of dimensional characteristics. A three dimensional representation of the dimensional and occurrence characteristics can be displayed in real time, such that the displayed three-dimensional representation can be continuously updated and further entries can be accumulated on the display as image analysis is performed.

As discussed previously, the three dimensional representation can be in tabular form or, more preferably, is in a plot having three coordinates such that two of the coordinates correspond to particle dimensional characteristics and a third coordinate corresponds to an occurrence characteristic. For example, the dimensional characteristics can include particle length, width, depth, diameter, sphericity, and aspect ratio. The occurrence characteristic can include a number, volume or area of particles having a matching set of dimensional characteristics or a total particle length, width, depth, diameter, sphericity or aspect ratio of particles having a matching set of dimensional characteristics. Preferably, the image analyzing unit includes an image analysis computer software program that creates and stores a matrix table which provides retrievable shape information for each particle in the still image. Thus, the set of actual dimensions, as measured, of each particle should be preserved for subsequent representation in the display.

Importantly, the three dimensional representation according to the present invention should provide information of the particles in a manner which permits a viewer to quickly, if not substantially instantaneously, determine a shape distribution of the particles appearing in the image. As stated previously, the display should begin to accumulate information as soon as a first image is taken so that the shape and size information is delivered quickly to a viewer in a format that can be readily comprehended in a minimum of time.

By way of example, and not by way of limitation, a commercially available prior art RapidVUE™ particle shape and size analyzer marketed by Beckman Coulter, Inc., Miami, Fla., can be utilized as the hardware for practicing the present invention. The RapidVUE™ particle shape and size analyzer is a computer controlled apparatus in which particles are passed in front of a camera and images of the particles are taken. The images are a continuous tone (grayscale) form and are converted to a digital form via sampling and quantization processes. The apparatus is thereby capable of measuring the dimensions of each particle appearing in the images. According to the present invention, however, the software of the prior art RapidVUE™ particle shape and size analyzer is modified such that the modified software creates and stores a matrix table of information correlating and preserving the dimensional characteristics of each particle and determines the occurrence value of the particles which meet pre-defined dimensional characteristics. Thus, the number or some other occurrence value can be determined for particles having a given shape and size, and a three dimensional representation can be displayed, as illustrated in FIGS. 4 and 6, to quickly reveal an accurate particle shape distribution within the sample.

Therefore, the apparatus and method according to the present invention provides a highly accurate means of quickly obtaining a shape and size distribution of particles within a sample. This information is particularly critical when two or more types of particle shapes are present within the sample. The present invention provides significantly more accurate and useable information than that of the prior art even when utilizing substantially the same measurement hardware. The prior art representations provide only smeared and separated particle dimensional distributions that do not reveal distribution of particle shape in a graphical display. In contrast, the present invention preserves shape information of each particle and displays the information three dimensionally to differentiate shape among particles in the sample.

Various modifications, alterations and changes may be made to the embodiments of the apparatus and method disclosed herein. For example, the fluid medium can be gas, air, or a liquid, and the particles can be of any particulate material including, for instance, materials utilized as fillers in paper, pharmaceuticals, cement, paint and other products. The image detector can be a video camera, a digital camera, or some other device for capturing an image. In addition, the image can be an optically taken image or an electronically taken image. Further, the display can be a print-out, a screen of a monitor or like electronic device, or some other means for projecting a display.

While a preferred apparatus and method have been described in detail, various modifications, alterations, and changes may be made without departing from the spirit and scope of the apparatus and method according to the present invention as defined in the appended claims.

What is claimed is:

1. Apparatus for analyzing particles suspended in a fluid medium, comprising:
    an image detector for obtaining at least one still image of a plurality of particles suspended in a fluid medium;
    an image analyzing unit for measuring from said at least one still image at least two dimensional characteristics per particle for each of said plurality of particles appearing in said at least one still image and for determining an occurrence characteristic of particles which is related to the particles having a matching set of measured dimensional characteristics; and
    a display unit for presenting a three dimensional representation of said measured dimensional characteristics and said occurrence characteristics of all said plurality of particles appearing in said image and providing information about said plurality of particles in a manner which permits a viewer of said three dimensional representation to determine a size and shape distribution of said plurality of particles appearing in said at least one still image.

2. An apparatus according to claim 1, wherein said display unit has a screen on which said three dimensional representation is provided as an x-y-z coordinate plot, and wherein two of said coordinates correspond to said dimensional characteristics and a third coordinate corresponds to said occurrence characteristic.

3. An apparatus according to claim 2, wherein said plot is continually updated in real-time such that said plot continues to accumulate and display further information as said at least one still image is processed by said image analyzing unit.

4. An apparatus according to claim 1, wherein at least one of said dimensional characteristics is selected from a group consisting of particle length, width, depth, diameter, sphericity, and aspect ratio.

5. An apparatus according to claim 1, wherein said occurrence characteristic is measured in terms of a parameter selected from a group consisting of particle number, particle area, particle volume, particle length, particle width, particle depth, particle diameter, particle sphericity, and particle aspect ratio.

6. An apparatus according to claim 1, wherein said image analyzing unit forms and stores a matrix table of data including at least said set of dimensional characteristics and said occurrence characteristics so that individual characteristics of each particle are saved and capable of representation in said three dimensional representation.

7. An apparatus according to claim 6, wherein said image analyzing unit is a computer having at least one image analysis computer software program which analyzes the still image, forms said matrix table, and causes said three dimensional representation to be displayed on said display unit.

8. An apparatus according to claim 1, further comprising a flow cell providing a path of flow for particles suspended in a fluid and defining a chamber in which said at least one still image is obtained by said image detector.

9. An apparatus according to claim 8, wherein said image detector is a camera for obtaining an optical image of said plurality of particles.

10. An apparatus according to claim 1, wherein one of said measured dimensional characteristics is particle depth.

11. An apparatus according to claim 1, further comprising a light source for directing a beam of light onto said plurality of particles when said image is obtained, said light source being positioned relative to said image detector such that said beam of light is directed substantially perpendicular to a direction in which said image is taken from said image detector.

12. Apparatus for analyzing particles suspended in a fluid, comprising:
    a flow cell having a chamber providing a path of flow for particles suspended in a fluid;
    a camera for obtaining at least one optical image of a plurality of particles located within said chamber;
    a computer system in communication with said camera for enabling said at least one optical image to be analyzed, said computer including at least one image analysis computer program for measuring at least two dimensional characteristics per particle for each of said particles appearing in said image and determining an occurrence characteristic of particles having a matching set of measured dimensional characteristics; and
    a monitor screen for displaying a three dimensional representation in real-time of said measured dimensional characteristics and said occurrence characteristics of all said plurality of particles appearing in said image as said characteristics are determined, said three dimensional representation having three coordinates such that two of said coordinates correspond to said measured dimensional characteristics and a third coordinate corresponds to said occurrence characteristic;

whereby said three dimensional representation provides information of said plurality of particles in a manner which permits ready determination of a size and shape distribution of said plurality of particles appearing in said at least one image.

13. An apparatus according to claim 12, wherein at least one dimensional characteristic set is selected from a group consisting of particle length, width, depth, diameter, sphericity, and aspect ratio.

14. An apparatus according to claim 13, wherein said occurrence characteristic is measured in terms of a parameter selected from a group consisting of particle number, particle area, particle volume, particle length, particle width, particle depth, particle diameter, particle sphericity, and particle aspect ratio.

15. An apparatus according to claim 14, wherein said camera is a CCD camera and said image is a still image.

16. A method of analyzing particles suspended in a fluid medium, comprising the steps of:
obtaining at least one still image of a plurality of particles suspended in a fluid medium;
measuring at least two dimensional characteristics per particle for each of said plurality of particles appearing in said image;
determining an occurrence characteristic of particles having a matching set of measured dimensional characteristics; and
displaying a three dimensional representation of said measured dimensional characteristics and said occurrence characteristics of all said plurality of particles appearing in said image, said three dimensional representation having three coordinates such that two of said coordinates correspond to said measured dimensional characteristics and a third coordinate corresponds to said occurrence characteristic such that said three dimensional representation provides information of said plurality or particles in a manner which permits a viewer to determine a size and shape distribution of said pluarality of particles appearing in said at least one image.

17. A method according to claim 16, wherein said measuring step is performed by an image analysis computer program after said at least one still image is obtained, and wherein said three dimensional representation is updated in real time as said image analysis computer program measures said dimensional characteristics.

18. A method according to claim 17, further comprising the step of forming a matrix table which correlates and stores said measured at least two dimensional characteristics and said associated occurrence characteristic.

19. A method according to claim 17, wherein said dimensional characteristic includes at least one parameter selected from a group consisting of particle length, width, depth, diameter, sphericity, and aspect ratio, and wherein said occurrence characteristic is measured in terms of a parameter selected from a group consisting of particle number, particle area, particle volume, particle length, particle width, particle depth, particle diameter, particle sphericity, and particle aspect ratio.

20. A method according to claim 19, further comprising the step of providing a path of flow for said plurality of particles suspended in the fluid, wherein said path of flow provides a location for obtaining said at least one still image.

21. A method according to claim 20, wherein said step of obtaining at least one still image is accomplished utilizing a camera to obtain an optical image.

22. A method according to claim 16, further comprising the step of directing a beam of light in a direction onto said plurality of particles in the fluid, and wherein said image is taken from a direction substantially perpendicular to the direction of the beam of light.

* * * * *